United States Patent [19]

Genshaw

[11] Patent Number: 5,208,142

[45] Date of Patent: May 4, 1993

[54] METHOD FOR SEPARATING ERYTHROCYTES FROM WHOLE BLOOD

[75] Inventor: Marvin A. Genshaw, Elkhart, Ind.

[73] Assignee: Miles Inc., Elkhart, Ind.

[21] Appl. No.: 794,483

[22] Filed: Nov. 19, 1991

[51] Int. Cl.$^5$ ............................................. G01N 21/22
[52] U.S. Cl. ............................................. 435/2; 436/63; 436/71; 436/86; 436/175; 436/177; 436/825; 210/696; 210/729; 435/11
[58] Field of Search ............... 435/2, 11; 436/63, 71, 436/86, 87, 88, 175, 177, 825; 210/696, 749, 767, 729

[56] References Cited

U.S. PATENT DOCUMENTS

| | | | |
|---|---|---|---|
| 3,552,925 | 7/1967 | Fetter | 436/169 |
| 3,733,179 | 8/1968 | Guehler | 436/71 |
| 4,211,531 | 7/1991 | Das | 436/71 |

Primary Examiner—James C. Housel
Assistant Examiner—David Redding
Attorney, Agent, or Firm—Jerome L. Jeffers

[57] ABSTRACT

A method for separation of erythrocytes from whole blood by diluting the whole blood with saline and introducing low concentrations of soluble salts of trivalent cations into the diluted blood sample.

10 Claims, No Drawings

METHOD FOR SEPARATING ERYTHROCYTES FROM WHOLE BLOOD

BACKGROUND OF THE INVENTION

There are available to the clinical analyst various test devices for the rapid analysis of certain constituents in blood samples which if found to be in excess of a predetermined concentration indicate a potential pathological condition. Such tests include means for detecting glucose and other sugars such as galactose. Other constituents normally present in blood samples include higher molecular weight materials such as albumin, cholesterol and triglycerides.

Many of the tests and methods for blood analysis have encountered difficulties when whole blood is analyzed because the test devices utilize chromogenic or other visual responses to indicate the presence or absence of the constituents being sought and the presence of red coloration in whole blood interferes with these colormetric determinations. In addition, for analytes other than hemoglobin, the concentration within the erythrocyte may be different from the plasma concentration. Accordingly, rupture of the erythrocytes may introduce undesirable changes into the assay results. This can be problematical in assay techniques which employ responses other than the formation of chromogens, such as those involving precipitation and enzyme catalyzed reactions.

Various techniques have been developed for separating erythrocytes from whole blood samples to provide blood plasma which can be analyzed without their interference. These methods typically involve precipitation and filtration in which various means for enhancing the separation are employed. One such means is disclosed in U.S. Pat. No. 3,552,925 in which there is described contacting a whole blood sample with a water soluble salt containing an inorganic cation to thereby enhance the separation of erythrocytes from the liquid fraction. The salts disclosed are primarily those having mono- or divalent cations although in one instance ferric chloride at a concentration of 1 molar is mentioned. In all cases, the salt is employed at a concentration in the range of from ¼ molar to saturation except in one embodiment of the system disclosed in which pieces of filter paper are immersed with a solution containing from 1 to 60% by weight of the salt and subsequently dried to leave a salt residue. This system works well when the blood is to be analyzed for low molecular weight highly soluble analytes such as glucose, however, higher molecular weight analytes such as cholesterol are separated along with the erythrocytes leaving a plasma sample which is unsuitable for the analytical determination of these high molecular weight analytes.

In German published patent application 34 41 149 there is disclosed a method for separating erythrocytes from diluted blood by the use of lectin. This process involves placing the blood sample on a matrix impregnated with lectin and separating the erythrocytes by thorough rinsing with a diluent.

It would be desirable and it is an object of this invention to provide a method for the separation of erythrocytes from whole blood using dilute salt solutions which will agglutinate erythrocytes without the concomitant precipitation of high molecular weight analytes.

SUMMARY OF THE INVENTION

The present invention involves a method of separating erythrocytes from whole blood to provide a blood plasma sample suitable for colormetric analysis of high molecular weight analytes. The method comprises the steps of:

a) diluting 1 part of the whole blood with at least 3 parts of a saline solution which is in osmotic balance with the whole blood sample, and b) contacting the diluted blood with a soluble salt of an anion and a trivalent cation wherein there is provided an amount of salt sufficient to provide a concentration thereof of from abut 0.1 to about 40 millimoles per liter to thereby cause erythrocytes to separate from the whole blood to provide a resultant blood plasma which is devoid of erythrocytes but which contains high molecular weight analytes as solutes therein.

DESCRIPTION OF THE INVENTION

The various methods which have been used to separate the cellular and liquid components of blood for analysis typically involve solid/liquid separatory techniques such as centrifugation or filtration. When filtration is to be used for the separation various method of enhancing the separation have been disclosed. The present invention can be used with either centrifugal or filtration separatory methods. Alternatively, the agglutinated erythrocytes can be allowed to separate from the blood's liquid phase by gravitational forces.

The present invention is predicated on the discovery that soluble salts of trivalent cations can at very low concentrations cause the agglutination and consequent separation of erythrocytes contained in whole blood. This is significant because the procedure permits the analyst to remove erythrocytes from whole blood without causing the concomitant precipitation of high molecular weight blood fractions, particularly cholesterol.

The disadvantage of the use of concentrated salt solutions is that they precipitate the protein and lipid fractions of the sample along with the erythrocytes to produce a protein and lipid free sample. This is satisfactory for the measurement of low molecular weight, highly soluble analytes such as glucose. However, important analytes such as albumin, cholesterol and triglycerides are absent from the plasma sample. This invention provides a means for separating erythrocytes from whole blood while avoiding the precipitation of high molecular weight analytes, particularly cholesterol, therefrom.

In carrying out the present invention it is essential that the whole blood be diluted with saline solution by at least a ratio of 3 parts saline to 1 part blood. A ratio of 8 to 30 parts saline to 1 part blood is preferred. Higher ratios can be employed, but are not necessary. The diluent should be a saline solution, preferable NaCl, which is osmotically approximately equal to that of blood. If the osmolity is significantly lower than that of blood, erythrocytes may rupture thereby contaminating the sample with intercellular components, whereas a significantly higher osmolity tends to draw water from the cells thereby diluting the sample and rendering the removal of crenated cells more difficult. One skilled in the art of blood fractionation will have no difficulty in preparing saline solutions of the appropriate concentration. The saline solutions used in the examples herein were of 0.85% w/v NaCl.

This invention is predicated on the discovery that red blood cell agglutination in diluted whole blood can be accomplished by contacting it with low concentrations of soluble salts of trivalent cations. While one might expect higher concentrations of these salts to result in erythrocyte agglutination, it is unexpected that this could be achieved using very low concentrations of the salts and that at such low concentrations the coprecipitation of high molecular weight analytes such as cholesterol can be avoided. In order to achieve this desirable result, the concentration of the trivalent salt in the diluted blood sample should be in the range of from about 0.1 to about 40 preferably 1 to 30 millimoles per liter. In order to minimize the precipitation of high molecular weight analytes the lowest concentration capable of causing erythrocyte agglutination should be employed. This concentration will vary slightly depending on the particular cation involved, however, the optimal concentration for any particular trivalent cation can readily be determined by one skilled in the art.

Suitable trivalent cations include chromium, scandium, yttrium, cobalt, titanium, and osmium. Trivalent aluminum, iron and lanthanum are particularly suitable due to their low cost and availability. The selection of the salt's anion is not critical provided that it does not form an insoluble salt with other cations present in the diluted blood sample. In this regard, the halogens, particularly chloride, anions are preferred.

Erythrocyte separation can be achieved in several different ways in accord with the present invention. For example, the whole blood can be diluted with the trivalent salt solution whereupon time and gravity or centrifugation will separate the cells from the plasma. The supernate of diluted plasma can then be removed by decantation or aspiration and assayed. In another embodiment the blood can be diluted with the salt solution and, upon agglutination, the erythrocytes can be removed by filtration whereupon a cell free filtrate is provided. Alternatively, the blood sample, after dilution, can be filtered through a filter impregnated with the salt to obtain the erythrocyte free filtrate. In each embodiment, dilution of the whole blood sample is essential, since absent such dilution agglutination of erythrocytes does not occur at these low salt concentrations possibly due to the removal of trivalent cations by absorption to the red cells or precipitation of the trivalent cation by blood components in the form of $MOH_3$ or $M^{3+}$ protein.

The method of practicing the present invention is further illustrated by the following examples:

EXAMPLE I

In this experiment 16 microliters of whole blood were combined with 500 microliters of the salt solution being tested. The test salt was dissolved in a saline solution (0.85 w/v % NaCl) in amounts sufficient to provide test salt concentrations in the diluted blood samples of from 0.2 mM to 1000 mM in increments of factors of 2.

After mixing, agglutination of the blood sample was determined by visually observing the agglutination of cells and their rapid settling.

The salts tested provided the following results:

$LaCl_3$—Agglutination was observed over a range of 2 to 15 mM concentration of the test salt in the diluted blood sample.

$FeCl_3$—Agglutination was observed over a range of 0.5 to 12 mM concentration.

$AlCl_3$—Agglutination was observed over a range of from 0.3 to 10 mM concentration.

$CaCl_2$—No agglutination was observed over a range of from 0.4 mM to 1 M.

From the above data, it can be determined that agglutination can be achieved at much lower concentrations with the use of salts of trivalent cations than is the case with salts of bivalent cations typically used in the prior art.

The cell free supernates were collected and tested for cholesterol content by means of a Seralyzer ® reagent strip.

In the case of the $LaCl_3$ treated blood, the cholesterol test gave negative results for the plasma treated with a salt concentration of from 30 to 500 mM. However, this test gave positive results for serum samples prepared using salt concentrations of 0, 4 mM, 15 mM and 20 mM.

In the case where aluminum chloride was used to separate erythrocytes from the blood, the cholesterol test was negative at salt concentrations of from 50 mM to 1 M whereas a positive response was achieved with the plasma which was treated with $AlCl_3$ concentrations of 0, 3 mM, 16 mM and 30 mM.

From the above experimental data, it can be determined that through careful control of the concentration of trivalent salt with which the blood sample is contacted one can cause agglutination of the erythrocytes while leaving the cholesterol in the sample unaffected.

EXAMPLE II

In this experiment filter paper (Whatman 31ET) was impregnated with the test salt by immersion in the salt solution followed by thorough drying. The salt concentration was increased from 1 to 1000 mM by factors of 2 for subsequent runs of this experiment. Whole blood diluted 1:8 with saline was poured through the filter paper and the agglutination of erythrocytes therein determined by visual observation of the zone beyond the area of the blood sample application which was wetted by the clear fluid migrating away from it.

The best separation for filter paper impregnated with $LaCl_3$ was at a salt concentration of 8 mM, 16 mM and 500 mM. While good erythrocyte separation was achieved at a concentration of 500 mM, this is too concentrated for the present invention due to the coprecipitation of cholesterol which results from the use of concentrated salts.

In a similar experiment it was determined that the best separation with $AlCl_3$ as the test salt occurred with filter paper impregnated with 4 mM to 30 mM solutions.

EXAMPLE III

Whole blood is diluted 1:30 with 0.85% w/v NaCl and 0.0001 N citric acid to avoid any possible precipitation of ferric hydroxide upon addition of ferric chloride as the source of ferric ion. Ferric chloride is added to provide a concentration ranging from 0.05 to 1000 millimolar incrementally increasing the concentration by factors of 2.

Agglutination of erythrocytes is observed over the range of 0.5 to 30 millimolar. After passing the treated blood sample through Whatman 31ET filter paper to remove the red blood cells, the filtrate tests positive for cholesterol over the range of 0.5 to 30 millimolar ferric chloride.

EXAMPLE IV

Several of the salts of monovalent cations as disclosed in the previously cited U.S. Pat. No. 3,552,925 were tested using the procedure of Example II. These salts were used in higher concentrations in order to achieve erythrocyte agglutination, i.e. 0.5 to 2 M since, as taught by the '925 patent and confirmed by Example I herein, there is required a much higher concentration of a mono or divalent cation than is the case with the salts of trivalent cations which are used in the present invention. The salts employed, their concentration in the solution used to treat the filter paper and the results observed are set out in Table I.

TABLE I

| Salt | Concentration | % Clear Liquid* |
|---|---|---|
| $NaBO_4$ | 0.5M | 5 |
| $K_2SO_4$ | 0.7M | 50-100 |
| NaCl | 1M | 5-25 |
| NaCl | 2M | 60-75 |
| $(NH_4)_2SO_4$ | 1M | 25-40 |
| $(NH_4)_2SO_4$ | 2M | 25-60 |
| K Br | 1M | 30-70 |
| K Br | 2M | 40-80 |
| $Na_2SO_4$ | 1M | 10-30 |
| $Na_2SO_4$ | 2M | 75-80 |

*The % clear liquid is the fraction of the filter paper containing clear fluid of the total area covered by the blood sample.

From the data of Table I it can be determined that even at these higher concentrations, only partial separation of erythrocytes was obtained. More significantly, in the case of each salt tested the subsequent test for cholesterol and other high molecular weight analytes, e.g. hemoglobin, leucocytes, triglycerides, was negative indicating that a gross precipitation effect is occurring under the conditions of this prior art method. Since ammonium sulfate, whose use is a classical method of precipitating proteins from blood is one of the salts suggested by the '925 patent, it is consistent with the results presently observed to conclude that the intent of the patentees therein was to provide a gross precipitation method in which high molecular weight analytes would be separated from the whole blood leaving only low molecular weight analytes such as glucose, potassium, chloride and uric acid remaining in the blood plasma. Separating erythrocytes by the technique of the present invention provides a plasma sample which retains high molecular weight analytes such as cholesterol, so that theirs presence in the serum sample can be colormetrically determined.

What is claimed is:

1. A method of separating erythrocytes from a whole blood sample to provide a blood sample serum suitable for colormetric analysis of cholesterol which comprises:

a) diluting 1 part of the whole blood sample with at least 3 parts of a saline solution which is in osmotic balance with the whole blood, and
    b) contacting the diluted blood sample with a soluble salt of an anion and a trivalent cation wherein the salt is present in an amount sufficient to provide a concentration of said salt in the diluted whole blood sample of from about 0.1 to about 40 millimoles per liter to thereby cause erythrocytes to agglutinate and separate from the whole blood sample to provide a resultant blood plasma sample which is devoid of erythrocytes but which contains a significant amount of high molecular weight analytes originally present in the sample.

2. The method of claim 1 wherein the blood sample is diluted by a ratio of 8 to 30 parts saline to 1 part of blood.

3. The method of claim 1 wherein the cation is chromium, scandium, yttrium, cobalt, titanium, osmium or a mixture thereof.

4. The method of claim 1 wherein the cation is aluminum, iron or lanthanum or a mixture thereof in the trivalent state.

5. The method of claim 1 wherein the agglutinated erythrocytes are separated from the diluted blood sample by settling and decantation or filtration.

6. In the method of analyzing a whole blood sample for the presence of cholesterol, the improvement which comprises diluting the blood sample with at least about 3 times the sample's volume of a saline solution which is in substantial osmotic balance with the blood in said sample and adding to the diluted blood sample a soluble salt of an anion and a trivalent cation in an amount sufficient to cause agglutination of the erythrocytes in the blood sample without causing significant precipitation of cholesterol.

7. The method of claim 6 wherein the soluble salt is added to the diluted blood sample in an amount sufficient to provide a concentration of the trivalent cation therein of from about 0.1 to about 40 millimoles per liter of the trivalent cation.

8. The method of claim 6 wherein the cation is chromium, scandium, yttrium, cobalt, titanium, osmium or a mixture thereof.

9. The method of claim 6 wherein the cation is aluminum, iron, lanthanum or a mixture thereof.

10. A method for the preparation of a blood plasma sample which comprises diluting a whole blood sample with from about 8 to about 30 parts of a saline solution which is in essentially osmotic balance with the whole blood and introducing $FeCL_3$, $AlCl_3$, $LaCl_3$ or a mixture thereof in an amount which will provide about 0.1 to about 40 millimoles per liter of the trivalent cation of said salt in the diluted blood sample to thereby cause erythrocytes in the diluted blood sample to agglutinate while not significantly precipitating the cholesterol present in said blood sample.

* * * * *